US00PP28371P3

(12) United States Plant Patent
Olesen

(10) Patent No.: US PP28,371 P3
(45) Date of Patent: Sep. 12, 2017

(54) ***CLEMATIS* PLANT NAMED 'EVIPO047'**

(50) Latin Name: *Clematis viticella*
Varietal Denomination: Evipo047

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 56 days.

(21) Appl. No.: 14/756,248

(22) Filed: Aug. 20, 2015

(65) Prior Publication Data

US 2017/0055417 P1 Feb. 23, 2017

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS http://poulsenroser.com/media/63344/Clematis-2012-2013_Poulsen-Roser_LR_GBP.pdf, "Perfection by Poulsen Clematis Main varieties 2013."*
UPOV hit on clematis plant named 'Evipo047', QZ PBR 43279, published Dec. 15, 2014.*

* cited by examiner

*Primary Examiner* — Anne Grunberg

(57) ABSTRACT

A new *Clematis* plant with a compact growth habit, profuse, dark violet flowers, and continuous summer flowering. The variety successfully propagates from softwood cuttings and is suitable for cultivation in commercial nursery culture. This new and distinct variety has shown to be uniform and stable in the resulting generations from asexual propagation from vegetative cuttings.

2 Drawing Sheets

Botanical classification:
Genus: *Clematis.*
Species: *viticella.*
Variety denomination: 'Evipo047'.

SUMMARY OF THE CLAIMED PLANT

The present invention constitutes a new and distinct variety of *Clematis* plant which originated from a controlled crossing between the female seed parent, an un-named seedling, and the male pollen parent, an un-named seedling. Both parent varieties are non-patented.

The two parents were crossed during the summer of 2000 and the resulting seeds were planted the following winter in a controlled environment in Guernsey, Channel Islands, United Kingdom. The new variety named 'Evipo047' originated as a single seedling from the stated cross.

The new *clematis* plant may be distinguished from its female seed parent and male pollen parent by the following characteristics. The female seed parent is taller in growth height than the newly claimed plant. The male pollen parent is more compact than the newly claimed plant.

The objective of the hybridization of this *clematis* plant was to create a new and distinct variety for nursery culture with unique qualities such as:

1. Uniform and abundant dark violet flowers;
2. Vigorous and compact growth, making the variety suitable for container culture;
3. Improved disease resistance; and
4. Non-climbing growth habit.

This combination of qualities was lacking in *clematis* plants that were in commercial cultivation and the qualities have been substantially achieved in the new variety.

'Evipo047' was selected by Mogens N. Olesen and Raymond J. Evison in their *clematis* development program in the Channel Islands, United Kingdom in 2001. Asexual reproduction of 'Evipo047' by means of vegetative cuttings and traditional layering was first performed by Mogens N. Olesen and Raymond J. Evison in the nursery during the summer of 2001. This initial and subsequent asexual propagations have demonstrated that the characteristics of 'Evipo047' are true to type and are transmitted from one generation to the next.

BRIEF DESCRIPTION OF THE DRAWING

The accompanying color illustrations show as true as is reasonably possible to obtain in color photographs of this type the typical characteristics of the buds, flowers, leaves, and stems, of 'Evipo047'.

Specifically illustrated in FIG. 1 are open flowers, tepals detached, reproductive flower parts, flower bud, and a bare flowering stem.

Figure 1:
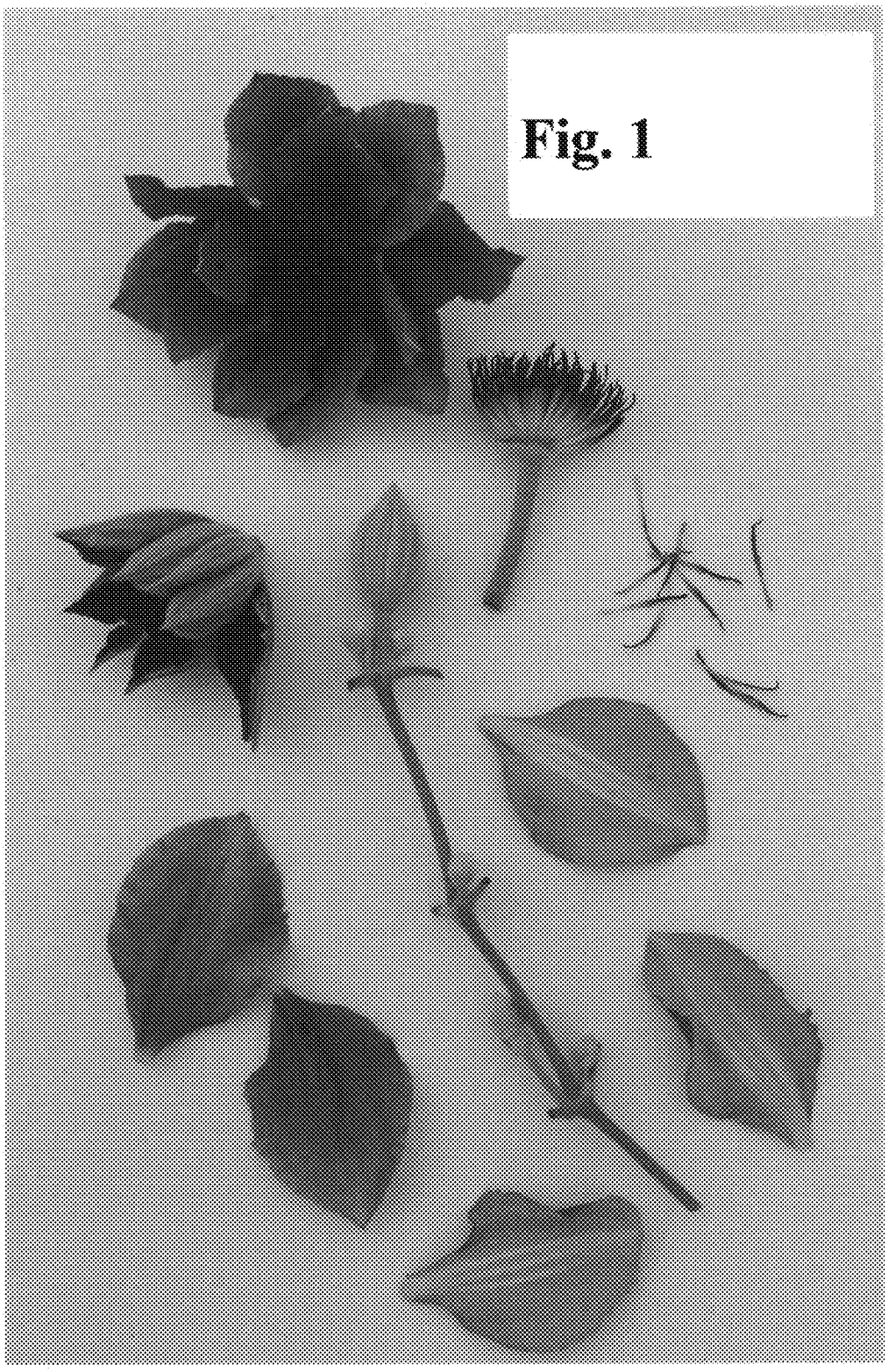
Figure 2:
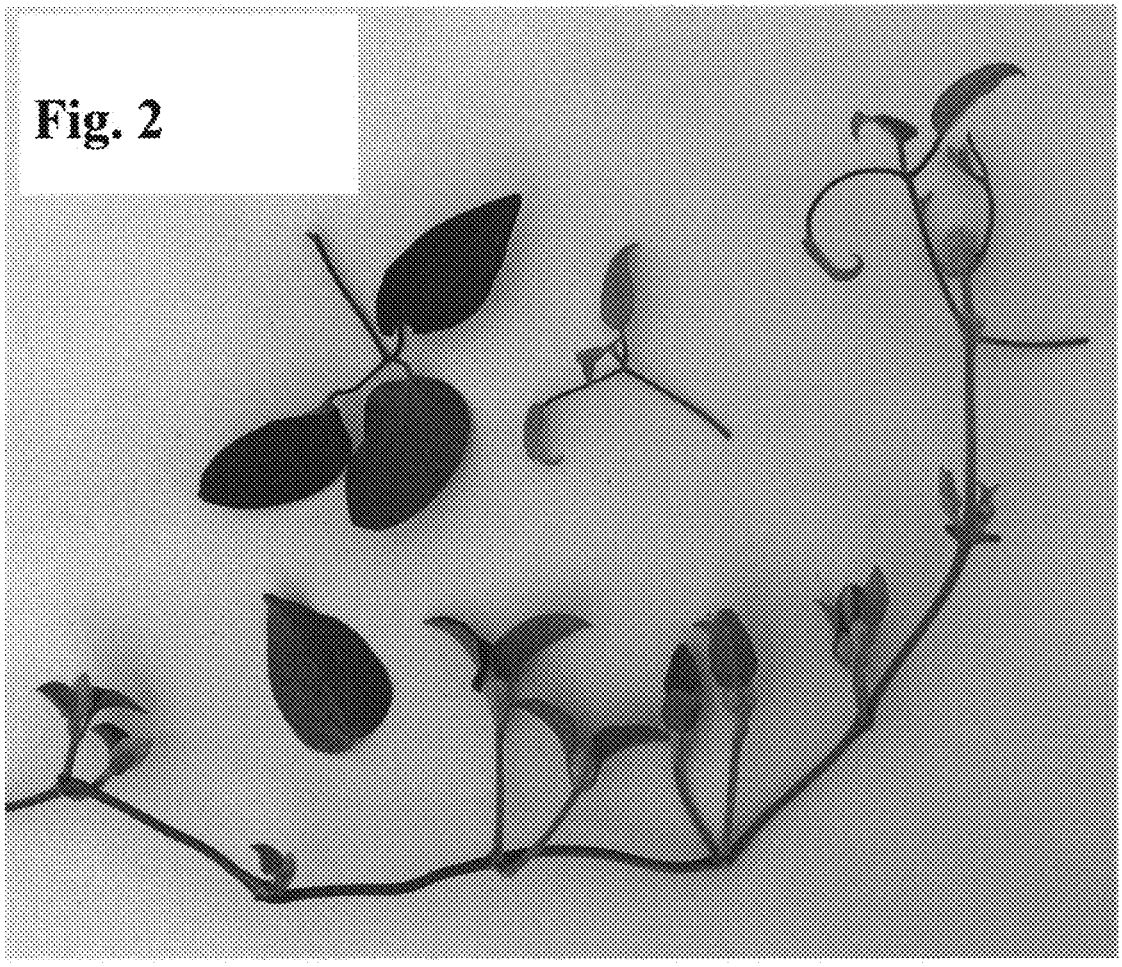

Illustrated in FIG. 2 are leaves and a bare stem exhibiting an abundance of axillary born flower buds. Plants shown are 2 years of age.

DETAILED DESCRIPTION OF THE VARIETY

The following is a detailed description of 'Evipo047', as observed in its growth throughout the flowering period in Yamhill County Oreg. Observed plants were cultivated for a period of 24 months in 2 liter containers. Certain phenotypical characteristics of the variety may vary under different environmental, cultural, agronomic, seasonal, and climatic conditions. Color references are made using The Royal Horticultural Society (London, England) Colour Chart, except where common terms of color are used.

For a comparison, several physical characteristics of the *clematis* variety 'Evipo026' described and illustrated in U.S. Plant patent application Ser. No. 13/986,920 are compared to 'Evipo047' in Chart 1.

CHART 1

| | 'Evipo047' | 'Evipo026' |
|---|---|---|
| Flower diameter | 80 mm | 90 mm |
| Tepal upper surface after opening | Violet Group N88C with intonations of Purple-Violet Group N81B | Violet-Blue Group N92B at margins with mid-tepal coloration of Violet-Blue Group 92A |
| Tepal count | 13 to 15 | 8 to 9 |

Flower and Flower Bud

Blooming habit: Continuous. The natural flowering period is generally from May to September.

Flower bud:
- *Size*.—Normally 30 mm in length. Bud diameter is 12 mm.
- *Bud form*.—Elliptic.
- *Bud color*.—Yellow-Green Group 145C.
- *Texture*.—Pubescent.

Peduncle:
- *Surface texture*.—Pubescent.
- *Length*.—On average 20 mm.
- *Diameter*.—4 to 5 mm.
- *Color*.—Yellow-Green Group 144B.
- *Strength*.—Strong.

Receptacle:
- *Surface texture*.—Pubescent.
- *Shape*.—Broad funnel.
- *Size*.—2 mm (h)×6 mm (w).
- *Color*.—Yellow-Green Group 144B.

Flower arrangement:
- *Location on vine*.—New and old growth.
- *Borne*.—At terminal and axillary buds.

Flower bloom:
- *Size*.—On average, flowers are 80 mm in diameter and 35 mm in depth.
- *Fragrance*.—None.
- *Lasting quality*.—Flowers normally remain up to 10 days on the plant.

Tepals:
- *Tepal color*.—The upper surface is Violet Group N88C with intonations of Purple-Violet Group N81B. The lower surface is Purple Group 76A with a central bar of Yellow-Green Group 145C.
- *Quantity*.—Normally 13 to 15 tepals.
- *Size*.—56 mm in length by 39 mm wide.
- *Shape*.—Individual tepal shape is elliptic. The tepal apex is acute. The tepal base acuminate.
- *Apex recurvature*.—None.
- *Tepal overlap*.—Partial.
- *Tepal cross section*.—Reflexed slightly.
- *Margins*.—Entire. Moderate undulations.
- *Persistence*.—Tepals drop off clean, easily.

Reproductive organs:
- *Arrangement*.—Open.
- *Pollen*.—None observed.
- *Anthers*.—Size: 10 mm in length. Color: Greyed-Purple Group Ni 86A. Quantity: On average, 55.
- *Filaments*.—Color: White Group 155C at base, towards apex is Red-Purple Group 68B. Length: 10 mm.
- *Pistils*.—Quantity: On average, 30.
- *Styles*.—Color: White Group 155A. Length: 15 mm.

Plant

Plant form: Spreading.

Plant growth: Seasons growth attains about 25 to 30 cm in height. Average spread is 50 cm.

Stems:
- *Color*.—Juvenile stems are Yellow-Green Group 144D. Mature stems are Greyed-Purple Group 183A.
- *Internodes*.—On average, 55 mm between nodes.
- *Length*.—Normally 15 cm from the base of the plant to the flowering portion of the stem.
- *Diameter*.—Normally 3 to 4 mm.
- *Texture*.—Pubescent.

Plant foliage:
- *Leaf characteristics*.—Deciduous.
- *Arrangement*.—Trifoliate.
- *Leaf size*.—Compound leaves are normally 110 mm (l)×110 mm (w). Leaflets are normally 50 mm (l)×32 mm (w).
- *Abundance*.—On average 2 leaves per 10 cm of stem.
- *Leaf color*.—Juvenile upper Yellow-Green Group N144B with marginal intonations of Red-Purple Group 185A. Juvenile lower Yellow-Green Group N144B. Mature upper Yellow-Green Group 146A. Mature lower Yellow-Green Group 147B.
- *Stipules*.—Absent.
- *Petioles*.—Size: Normally 40 mm in length by about 2 mm diameter. Texture: Smooth. Color: Greyed-Purple Group 183A.
- *Petioloule*.—Size: Normally 30 mm in length by 1 mm diameter. Texture: Smooth. Color: Greyed-Purple Group 183A.
- *Leaflet shape*.—Broad based ovate.
- *Margin*.—Entire.
- *Surface*.—The upper and lower sides are smooth.
- *Thickness*.—Moderate.
- *Glossiness*.—Not glossy.

Disease resistance: Subject to any disease that normally attacks the species. However the variety is more tolerant to *clematis* wilt, *Ascochyta clematidina*, than some *clematis* known to the inventors.

Cold hardiness: The variety is tolerant to USDA Hardiness Zone 6.

Heat tolerance: The variety has been found to be suitable for climate conditions found in the American Horticulture Society heat zone 7.

I claim:

1. A new and distinct variety of *clematis* plant named 'Evipo047', substantially as described and illustrated, due to its abundant dark violet flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *